(12) United States Patent
Dixon et al.

(10) Patent No.: US 8,905,019 B2
(45) Date of Patent: Dec. 9, 2014

(54) PATIENT CIRCUIT INTEGRITY ALARM USING EXHALED CO2

(75) Inventors: Paul David Dixon, Leytonstone (GB); Terry Lee Blansfield, Orange, CA (US)

(73) Assignee: Carefusion 207, Inc., San Diego, CA (US)

( * ) Notice: Subject to any disclaimer, the term of this patent is extended or adjusted under 35 U.S.C. 154(b) by 529 days.

(21) Appl. No.: 12/777,393

(22) Filed: May 11, 2010

(65) Prior Publication Data

US 2011/0277758 A1    Nov. 17, 2011

(51) Int. Cl.
| | | |
|---|---|---|
| *A61M 16/00* | (2006.01) | |
| *A61M 16/08* | (2006.01) | |
| *A61M 16/12* | (2006.01) | |
| *A61M 16/20* | (2006.01) | |
| A61M 16/06 | (2006.01) | |
| A61M 16/16 | (2006.01) | |
| A61M 16/10 | (2006.01) | |

(52) U.S. Cl.
CPC ... *A61M 16/0051* (2013.01); *A61M 2016/0036* (2013.01); *A61M 2016/0042* (2013.01); *A61M 2016/0021* (2013.01); *A61M 2016/0027* (2013.01); *A61M 16/06* (2013.01); *A61M 2205/583* (2013.01); *A61M 2230/432* (2013.01); *A61M 16/16* (2013.01); *A61M 16/0833* (2013.01); *A61M 16/12* (2013.01); *A61M 2016/0039* (2013.01); *A61M 2016/103* (2013.01); *A61M 2205/13* (2013.01); *A61M 2205/18* (2013.01); *A61M 16/209* (2013.01)
USPC .................................. 128/202.22; 128/204.22

(58) Field of Classification Search
USPC ............. 128/202.22, 204.21–204.23, 205.23; 244/118.5; 600/529, 532
See application file for complete search history.

(56) References Cited

U.S. PATENT DOCUMENTS

| | | | |
|---|---|---|---|
| 4,302,640 A | | 11/1981 | Vicenzi et al. |
| 5,063,938 A | * | 11/1991 | Beck et al. ..................... 600/537 |
| 5,319,355 A | * | 6/1994 | Russek ..................... 340/573.1 |
| 5,662,099 A | | 9/1997 | Tobia et al. |
| 5,881,717 A | * | 3/1999 | Isaza ........................ 128/202.22 |
| 6,041,777 A | * | 3/2000 | Faithfull et al. ........... 128/200.24 |
| 6,425,395 B1 | * | 7/2002 | Brewer et al. ............. 128/202.22 |
| 2002/0082511 A1 | * | 6/2002 | Carlebach et al. ............ 600/529 |
| 2002/0104536 A1 | * | 8/2002 | Richey, II ................ 128/204.22 |
| 2002/0185126 A1 | * | 12/2002 | Krebs ..................... 128/200.24 |
| 2005/0061321 A1 | * | 3/2005 | Jones ...................... 128/204.18 |
| 2005/0177055 A1 | | 8/2005 | Kuck et al. |
| 2005/0203432 A1 | | 9/2005 | Orr et al. |
| 2005/0279358 A1 | * | 12/2005 | Richey ..................... 128/204.23 |
| 2007/0028921 A1 | | 2/2007 | Banner et al. |
| 2007/0193581 A1 | | 8/2007 | Laurila et al. |
| 2008/0091117 A1 | * | 4/2008 | Choncholas et al. ......... 600/538 |
| 2009/0293877 A1 | * | 12/2009 | Blanch et al. ............. 128/204.23 |
| 2011/0277759 A1 | * | 11/2011 | Crutchfield .............. 128/202.22 |
| 2013/0255683 A2 | * | 10/2013 | Kapust et al. ............ 128/204.23 |

OTHER PUBLICATIONS

PCT Search Report and Written Opinion mailed Feb. 9, 2012, 10 pgs.
International Preliminary Report on Patentability, PCT/US2011/035899. Mailed Nov. 13, 2012.

* cited by examiner

*Primary Examiner* — Loan H Thanh
*Assistant Examiner* — Andrew S Lo
(74) *Attorney, Agent, or Firm* — McDermott Will & Emery LLP

(57) ABSTRACT

A carbon dioxide sensor for use in a respiratory therapy system. The carbon dioxide sensor determines whether a patient interface is fluidly coupled to a patient.

19 Claims, 5 Drawing Sheets

PATIENT CIRCUIT INTEGRITY ALARM USING EXHALED CO2

BACKGROUND

Lung ventilators provide therapeutic gas (e.g., oxygen) and pressure volume support to a patient's lungs in order to facilitate gas exchange with a patient, either by supporting spontaneous breathing or by providing mandatory ventilation in the absence of spontaneous breathing. The gas is provided to a patient through an inspiratory conduit and the ventilator is fluidly coupled to the lung using a patient interface such as an endotracheal tube, a nasal cannula or a mask. There is a risk that fluid connection from the ventilator to the lung may be lost, for example due to movement of the patient causing the patient interface to become dislodged. If the patient interface is disconnected from the patient, this loss of breathing can be harmful to the patient.

Current ventilators detect such loss of breathing by use of complex algorithms based on measurements of breathing circuit pressure and flow. These algorithms can be problematic in scenarios with significant leaks, such as are common in long term applications, or with high-resistance tubes such as narrow bore nasal cannulae. When a breathing tube is dislodged, it may remain occluded or partially occluded, for example, by resting against the patient's face, causing the alarm mechanism to fail. Still further, these complex algorithms can be difficult to implement within the ventilator. As a result, reliable detection methods and adequate sensitivity to breathing circuit integrity are desired.

SUMMARY

The present disclosure relates to a use of a carbon dioxide sensor to indicate whether a patient circuit is in fluid connection with a patient's lungs. In one aspect, a respiratory therapy system includes an inspiratory conduit and an expiratory port. A patient interface is fluidly coupled to the inspiratory conduit and the expiratory port. The patient interface is further configured to be coupled to a patient. A carbon dioxide sensor is fluidly coupled to the expiratory port and provides an indication of whether the patient interface is fluidly coupled to the patient.

In another aspect, a respiratory therapy system includes a ventilator configured to provide inhaled gas to a patient and receive exhaled gas from the patient. The respiratory therapy system also includes a carbon dioxide sensor determining an amount of carbon dioxide in the exhaled gas and comparing the amount to a threshold.

In yet another aspect, a method of providing respiratory therapy to a patient includes providing a patient interface configured to be fluidly coupled to the patient. Gas is provided to the patient interface through an inspiratory conduit and exhaled gas is received from the patient. An amount of carbon dioxide is measured in the exhaled gas and an indication of fluid coupling between the patient interface and the patient is provided as a function of the amount of carbon dioxide.

DETAILED DESCRIPTION

Figure 1:
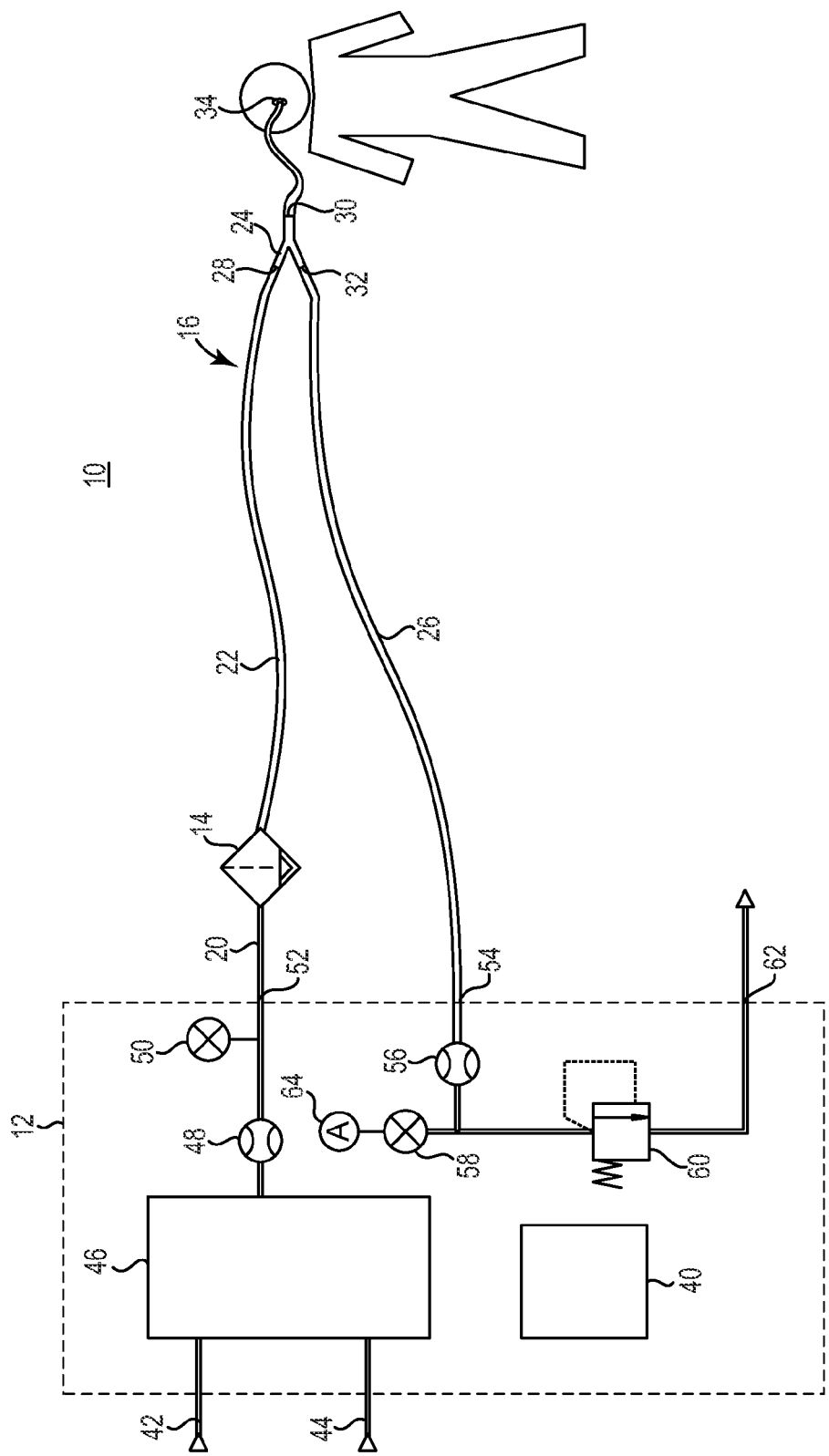
FIG. 1 is a schematic diagram of a first embodiment of a respiratory therapy system.

FIG. 1 is a schematic view of a respiratory therapy system 10 including a ventilator 12, an optional humidifier 14 and a patient circuit 16. It is worth noting that system 10 is one exemplary embodiment for concepts presented herein. For example, other forms of respiratory therapy can be used with the concepts presented herein such as a CPAP (Continuous Positive Airway Pressure) System or other system that may add or remove one or more of the components of system 10. In the embodiment illustrated, ventilator 12 supplies gases to humidifier 14 through an initial conduit 20. Humidifier 14 heats water within a humidification chamber to form water vapor, which mixes with gas provided by the ventilator 12, which is then output to patient circuit 16. Patient circuit 16 includes an inspiratory conduit (or limb) 22, a y-connector 24 and an expiratory conduit (or limb) 26. In alternative embodiments, for example, in a CPAP system, the y-connector 24 and/or expiratory conduit 26 can be eliminated. In other embodiments, humidifier 14 can be eliminated and thus the patient is provided with dry breathing gas.

Y-connector 24 includes an inspiratory port 28, a patient port 30 and an expiratory port 32. Inspiratory conduit 22 is fluidly coupled to the inspiratory port 28, so that gases from ventilator 12 are transferred from the inspiratory port 28 to the patient port 30. Patient port 30, in turn, is fluidly coupled to a patient interface 34 that is configured to be fluidly coupled to lungs of the patient. Exhaled gas from the patient is transmitted from patient interface 34 to expiratory port 32. Expiratory port 32 is fluidly coupled to expiratory conduit 26, which transmits exhaled gas back to ventilator 12. In one embodiment, patient interface 34 is an endotracheal tube. Other patient interfaces can include masks, nasal prongs, etc.

In one embodiment, ventilator 12 includes a controller 40 for operating the ventilator 12. For example, the controller 40 can provide several functions to monitor and control various parameters associated with respiratory therapy system 10. Such parameters include gas flow rate, gas temperature, carbon dioxide quantity, gas mixture percentages, etc. Additionally, ventilator 12 includes an air inlet 42 and a gas inlet 44 fluidly coupled to a gas mixing and flow delivery module 46. In one embodiment, controller 40 is configured to control gas mixing and flow delivery module 46 so as to provide a desired gas mixture to initial conduit 20. Air inlet 42 provides air to gas mixing and flow delivery module 46 whereas gas inlet 44 provides a gas such as oxygen to gas mixing and flow delivery module 46. Gas mixing and flow delivery module 46 mixes the gases from inlets 42 and 44 in order to provide a desired blend of gas. In other embodiments, ventilator 12 may operate solely with air, with a predetermined mixture of gas (e.g., a mixture of helium and oxygen) or operate with other gas inlet configurations. The desired blend of gas from mixing and flow delivery module 46 flows through a flow sensor 48 and a pressure sensor 50, which monitor the flow and pressure, respectively, of gas flowing to initial conduit 20. Flow sensor 48 and pressure sensor 50 can be coupled to controller 40 so as to provide data to controller 40 for control of ventilator 12. Initial conduit 20 is fluidly coupled to ventilator 12 at a gas outlet 52.

In one embodiment, ventilator 12 also receives exhaled air from the patient through expiratory port 32 and expiratory conduit 26, which can be fluidly coupled to ventilator 12 through a gas inlet 54. After entering ventilator 12, exhaled gas flows through a flow sensor 56 and a carbon dioxide sensor 58 to an exhaust valve 60, which can both be operably coupled to controller 40. Exhaust valve 60 can be operated to release gas from ventilator 12 through an exhaust 62 so as to maintain a desired pressure within patient circuit 16. Flow sensor 56 measures flow of air from the patient while carbon dioxide sensor 58 determines whether the patient circuit 16 is properly coupled to the patient, for example by comparing an amount of carbon dioxide in the exhaled air to a threshold. If the amount of carbon dioxide is below the threshold for a period of time, an alarm 64 can be operated (e.g., by controller 40). Carbon dioxide sensor 58 can be obtained from Alphasense Ltd., of Great Notley, United Kingdom, part IRC-A1, in one embodiment. In any event, the carbon dioxide sensor is fluidly coupled to expiratory port 32 so as to measure an amount of carbon dioxide from the patient.

Figure 2:
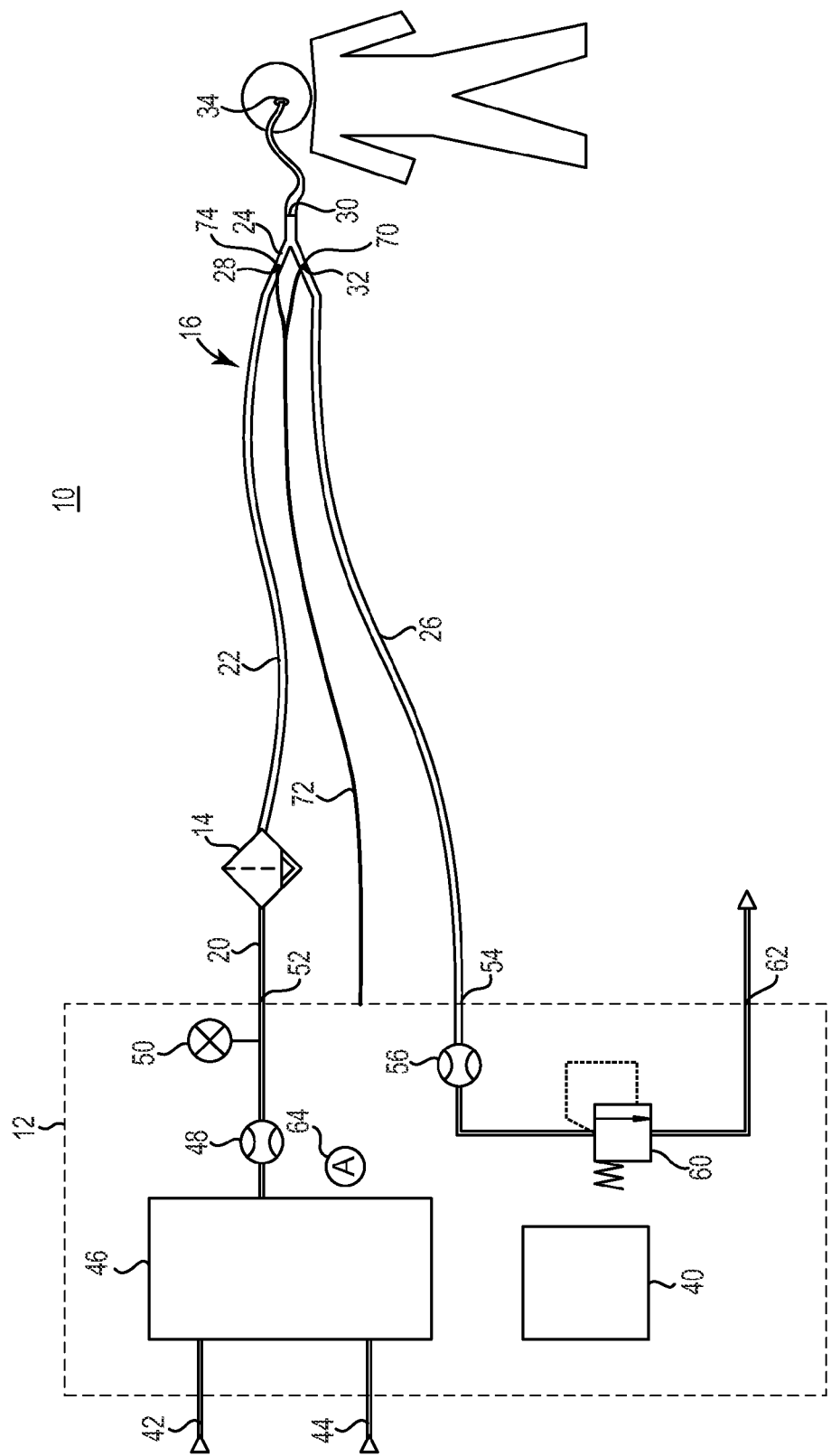
FIG. 2 is a schematic diagram of a second embodiment of a respiratory therapy system.

It is worth noting that in other embodiments, a carbon dioxide sensor need not be positioned directly within ventilator 12 and can be selectively positioned in various locations so as to be fluidly coupled to an expiratory port and receive exhaled gas from the patient. Moreover, multiple carbon dioxide sensors can be utilized in other embodiments. In one example illustrated in FIG. 2, a first carbon dioxide sensor 70 is positioned proximate the patient and fluidly coupled directly to expiratory port 32 and y-connector 24, the carbon dioxide 70 sensor being electrically coupled to the ventilator 12 through a cable 72. Carbon dioxide sensor 70 measures an amount of carbon dioxide in expiratory port 32 and provides the amount to ventilator 12. In one embodiment, the carbon dioxide sensor 70 can be coupled to controller 40. A second carbon dioxide sensor 74 is fluidly coupled to inspiratory port 28 to measure an amount of carbon dioxide in the inspiratory port 28. The respective measured values from sensors 70 and 74 can be compared by controller 40 to determine whether the patient circuit 16 is fluidly coupled to the patient.

Figure 3:
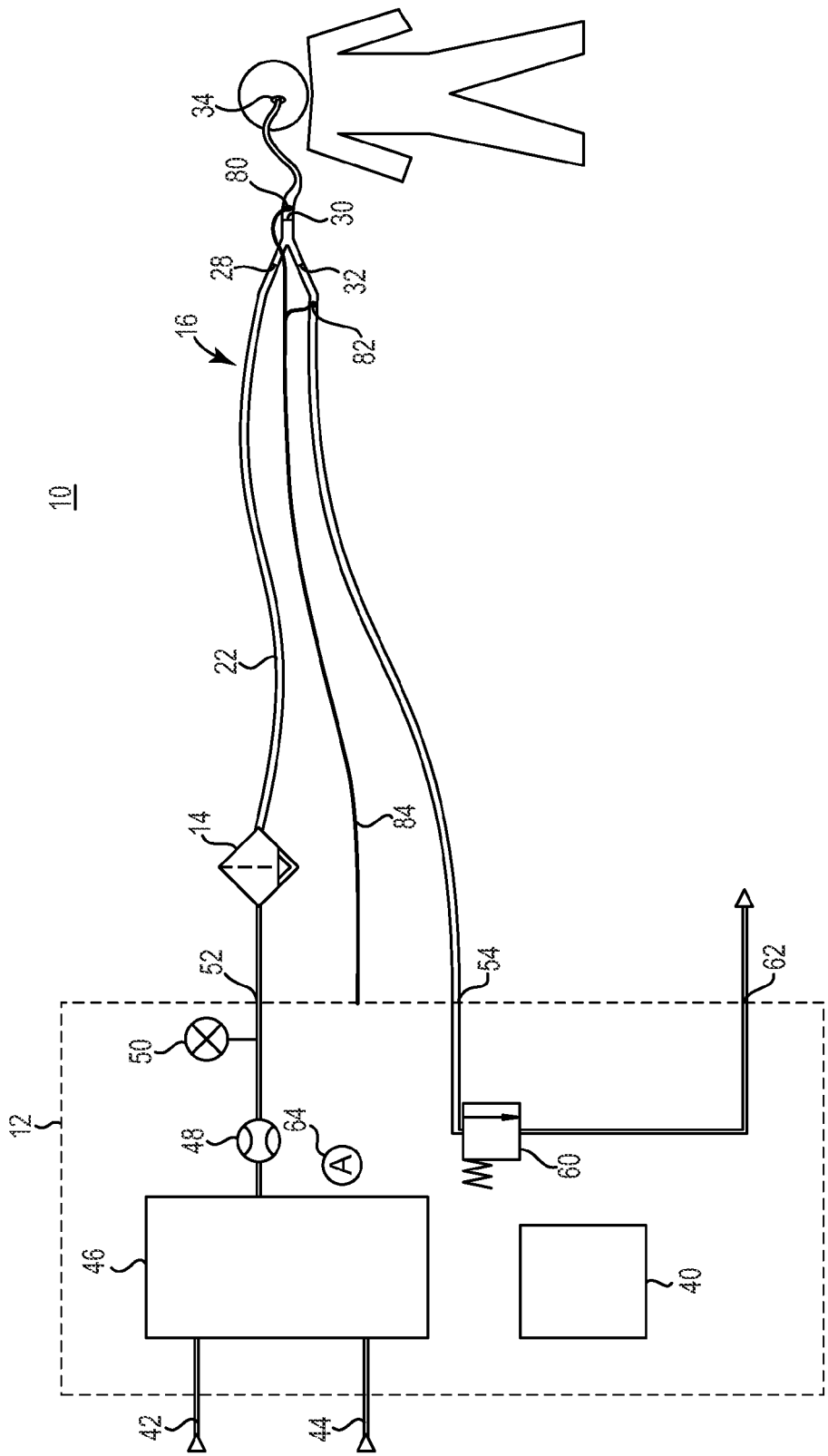
FIG. 3. is a schematic diagram of a third embodiment of a respiratory therapy system.

In another embodiment, illustrated in FIG. 3, a flow sensor 80 and a carbon dioxide sensor 82 are both fluidly coupled to expiratory port 32 proximate the patient. The carbon dioxide sensor 82 is coupled with the flow sensor 80 and measurements from the flow sensor 80 and carbon dioxide sensor 82 are provided to ventilator 12, and in particular controller 40, through a cable 84.

Figure 4:
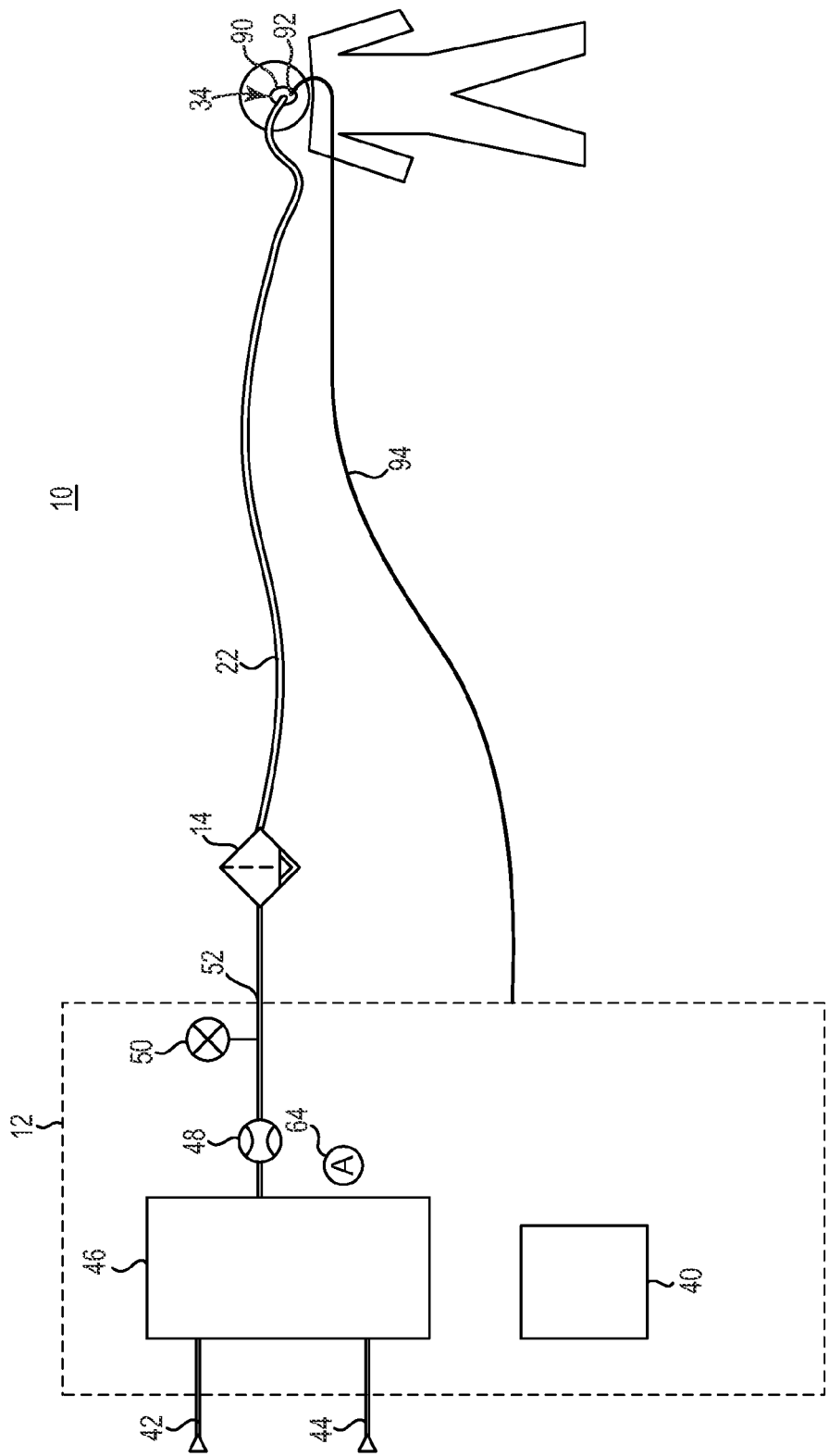
FIG. 4 is a schematic diagram of a fourth embodiment of a respiratory therapy system.
Figure 5:
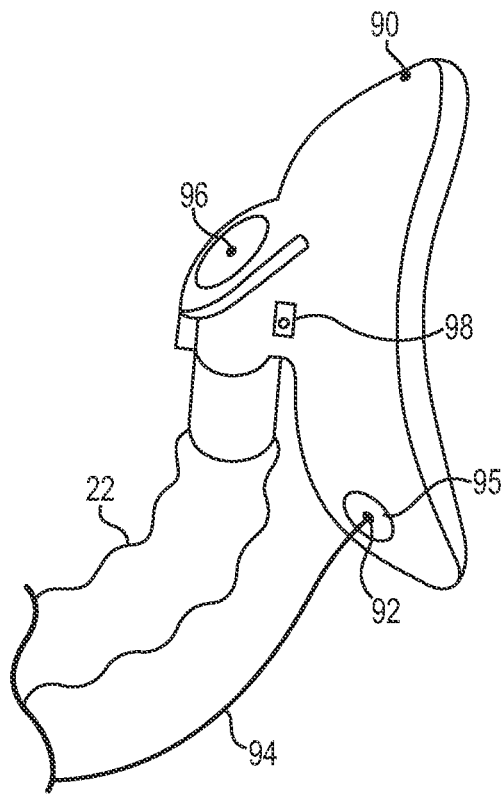
FIG. 5 is a schematic diagram of a mask having a carbon dioxide sensor coupled thereto.

In yet a further embodiment, illustrated in FIG. 4, patient interface 34 is embodied as a mask 90, wherein a carbon dioxide sensor 92 is directly affixed to the mask 90 and electrically coupled to ventilator 12 though a cable 94. Expiratory conduit 26 has been eliminated and exhaled gas is released from the mask 90 through an expiratory port integrated into the mask 90. Carbon dioxide sensor 92 directly measures an amount of carbon dioxide exhaled by the patient into the mask 90. FIG. 5 is a close-up view of mask 90, illustrating carbon dioxide sensor 92 and cable 94 coupled thereto. Carbon dioxide sensor is provided in an expiratory port 95 of mask 90. Mask 90 also includes a safety valve 96 for releasing pressure within mask 90. In a further embodiment, a photochemical carbon dioxide sensor 98 can provide further visual indication of mask 90 being fluidly coupled to the patient.

By fluidly coupling a carbon dioxide detector to an expiratory port, system 10, as illustrated in FIGS. 1-4 above, can detect if a patient interface is fluidly coupled to a patient. Exhaled gas from a patient includes higher amounts of carbon dioxide then ambient gas or inhaled gas within inspiratory conduit 22. Using a carbon dioxide sensor (e.g., sensors 58, 70, 74, 82, 92), for example a non-dispersive infrared sensor or electrochemical sensor, to analyze exhaled gas can detect presence or absence of carbon dioxide in order to provide a reliable detection for a loss of breathing circuit integrity. Stated another way, a low level of carbon dioxide for a period of time can indicate that a patient interface is not properly fluidly coupled to the patient. In one embodiment, the carbon dioxide concentration in the exhaled gas is measured by the carbon dioxide sensor and continuously compared with a threshold value. In the event that the concentration remains below a threshold value for a specified period of time, the alarm 64 (e.g., audible and/or visible) is operated to alert the caregiver. In one example, the alarm can include a red flashing lamp, an audible alarm, a textual message provided on a graphical interface and/or combinations thereof. If multiple carbon dioxide sensors are used (e.g., sensors 70 and 74) a differential value can be calculated between different carbon dioxide measurements. The differential value can further be compared to a threshold and alarm 64 operated if the value is below the threshold. In a further embodiment, a photochemical carbon dioxide detector (e.g., sensor 98) can be used to provide further visual indication of a patient interface being fluidly coupled to a patient's lungs.

Figure 6:
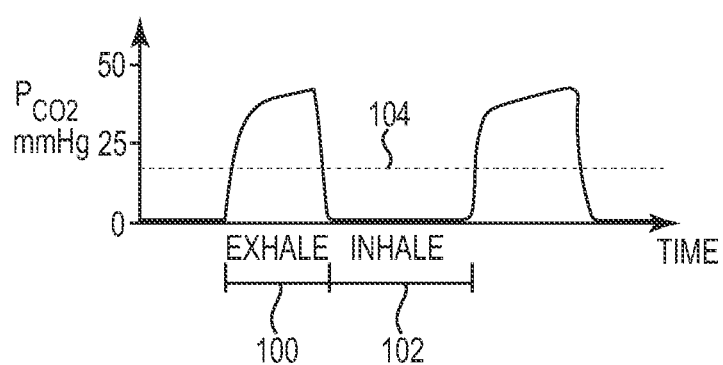
FIG. 6 is a graph of carbon dioxide measured from exhaled gas of a respiratory therapy system as a function of time.

FIG. 6 is a graph of an amount carbon dioxide measured as a function of time. In periods where the patient exhales, as denoted by period 100, the amount of carbon dioxide rises. In contrast, where the patient inhales, as denoted by period 102, the amount of carbon dioxide is reduced to a small amount. In some instances, it may be appropriate to use a fixed threshold carbon dioxide concentration, for example, within a range of 1,000 to 10,000 parts per million. An example threshold 104 is indicated in FIG. 6. One example threshold would be 1,500 parts per million (i.e., 0.15%). In other applications, an algorithm may be used to select a preferred threshold value. For example, when a size of the patient or a tidal volume of the patient is known and the biased flow rate (e.g., the flow rate of fresh breathing gas through the circuit during isolation, and intended to sweep exhaled gas from the circuit to prevent rebreathing) is known, a preferred threshold may be selected within the same range, allowing more rapid detection of disconnection.

The value for a specified period for detection of disconnection may either be a preset preferred value, such as 30 seconds or it may be longer or shorter and determined by a clinician using knowledge of a patient's physiological status. For example, a shorter interval such as 10 seconds may be appropriate in the case of a pre-term infant, who may sustain significant harm within 20 seconds of loss of respiratory support, or the value may be at longer intervals such as one minute for an adult patient requiring some additional support for spontaneous breathing.

In any event, in cases where the patient interface (e.g., tubing, cannula or mask) falls out of the patient's orifice and becomes partially blocked or occluded, detection of the leak can be provided by the carbon dioxide sensor. Additionally, by monitoring carbon dioxide, other highly dangerous situations such as obstruction of the trachea or main bronchus in a patient, cardiac arrest, etc., will also operate the alarm 64.

Although the present disclosure has been described with reference to preferred embodiments, workers skilled in the art will recognize that changes can be made in form and detail without departing from the spirit and scope of the present disclosure.

What is claimed is:

1. A respiratory therapy system, comprising:
   an inspiratory conduit;

an expiratory port;

a patient interface fluidly coupled to the inspiratory conduit and the expiratory port, the patient interface configured to be fluidly coupled to a patient;

a first carbon dioxide sensor fluidly coupled to the expiratory port and configured to determine a first amount of carbon dioxide in a first gas; and a second carbon dioxide sensor configured to determine a second amount of carbon dioxide in a second gas, wherein the first carbon dioxide sensor provides an indication of whether the patient interface is fluidly coupled to the patient based on a comparison between the first amount to the second amount.

2. The respiratory therapy system of claim 1, wherein the first carbon dioxide sensor measures an amount of carbon dioxide over a period of time and compares the amount to a threshold, the period of time being based on a characteristic of the patient.

3. The respiratory therapy system of claim 1, wherein the first carbon dioxide sensor is connected to the patient interface.

4. The respiratory therapy system of claim 1, wherein the first carbon dioxide sensor is connected to the expiratory port.

5. The respiratory therapy system of claim 1, further comprising:

a ventilator providing gas to the inspiratory conduit and receiving exhaled gas from the expiratory port through an expiratory conduit, wherein the first carbon dioxide sensor is connected to the ventilator.

6. The respiratory therapy system of claim 1, wherein the second carbon dioxide sensor is fluidly coupled to the inspiratory conduit.

7. The respiratory therapy system of claim 1, further comprising:

an alarm coupled to the first carbon dioxide sensor and configured to be operated if the first carbon dioxide sensor provides an indication that the patient interface is not fluidly coupled to the patient.

8. A respiratory therapy system, comprising:

a ventilator configured to provide inhaled gas to a patient and receive exhaled gas from the patient;

a carbon dioxide sensor configured to determine a first amount of carbon dioxide in the exhaled gas;

a second carbon dioxide sensor configured to determine a second amount of carbon dioxide in a second gas, different than the exhaled gas; and a controller operably coupled to the carbon dioxide sensor, the controller configured to compare the first amount to a threshold over a period of time and provide an indication of whether the ventilator is fluidly coupled to the patient based on the comparison, the controller further configured to compare the first amount to the second amount to determine a difference, and to compare the difference to a differential threshold.

9. The respiratory therapy system of claim 8, further comprising:

an inspiratory conduit;

an expiratory port;

a patient interface fluidly coupled to the inspiratory conduit and the expiratory port, the patient interface configured to be fluidly coupled to a patient; and wherein the controller operably coupled to the carbon dioxide sensor provides the indication based on whether the patient interface is fluidly coupled to the patient.

10. The respiratory therapy system of claim 9, wherein the carbon dioxide sensor is connected to the patient interface.

11. The respiratory therapy system of claim 9, wherein the carbon dioxide sensor is connected to the expiratory port.

12. The respiratory therapy system of claim 8, wherein the carbon dioxide sensor is connected to the ventilator.

13. The respiratory therapy system of claim 8, further comprising:

an alarm coupled to the carbon dioxide sensor and configured to be operated if the carbon dioxide sensor provides an indication that the first amount of carbon dioxide has been below the threshold for a period of time.

14. A method of providing respiratory therapy to a patient, comprising:

providing a patient interface configured to be coupled to the patient;

providing gas to the patient interface;

receiving exhaled gas from the patient;

measuring an amount of carbon dioxide in the exhaled gas over a period of time, wherein the period of time is based on a characteristic of the patient; and providing an indication of fluid coupling between the patient interface and the patient as a function of the amount of carbon dioxide.

15. The method of claim 14, wherein providing the indication further includes comparing the amount to a threshold.

16. The method of claim 14, further comprising:

providing a carbon dioxide sensor connected to the patient interface.

17. The method of claim 14, further comprising:

measuring a second amount of carbon dioxide in a gas other than the exhaled gas;

comparing the first-mentioned amount to the second amount; and determining if the patient interface is fluidly coupled to the patient as a function of the comparison.

18. The method of claim 14, further comprising:

operating an alarm if the patient interface is not fluidly coupled to the patient.

19. The method of claim 14, wherein the characteristic of the patient comprises at least one of an age of the patient or a health condition of the patient.

* * * * *